United States Patent [19]

Malcolm et al.

[11] Patent Number: 4,670,574

[45] Date of Patent: Jun. 2, 1987

[54] FORMATION OF ALKYLSILANES

[75] Inventors: Arcelio J. Malcolm; Charles R. Everly; Gunner E. Nelson, all of Baton Rouge, La.

[73] Assignee: Ethyl Corporation, Richmond, Va.

[21] Appl. No.: 908,736

[22] Filed: Sep. 18, 1986

[51] Int. Cl.$^4$ ............................................. C07F 7/08
[52] U.S. Cl. ...................... 556/478; 556/479; 556/481
[58] Field of Search ................................ 556/481, 479

[56] References Cited

U.S. PATENT DOCUMENTS

| | | | |
|---|---|---|---|
| 2,537,763 | 1/1951 | Hurd | 556/479 |
| 2,759,960 | 8/1956 | Nishikawa et al. | 556/481 |
| 3,065,253 | 11/1962 | Merritt | 556/481 X |

*Primary Examiner*—Paul F. Shaver
*Attorney, Agent, or Firm*—Donald L. Johnson; John F. Sieberth; Robert A. Linn

[57] ABSTRACT

Silane and monoalkylsilanes can be alkylated using an alkali metal aluminate, $MAlR_4$, wherein M is Li, Na, or K and each R is a straight chain, alkyl radical solely composed of carbon and hydrogen containing from about 4 to about 18 carbon atoms. The aluminate can be used as a reactant, optionally in the presence of a straight chain alpha-olefin corresponding to the alkyl group in the aluminate. Alternatively, the aluminate can be used as a catalyst for the reaction of the olefin and the silane reactant, in which case from about 5 to about 10 mole percent of the aluminate (based on the silane reactant) is employed. The catalytic reaction is promoted by a smaller amount of a lithium salt such as lithium chloride. Both embodiments are conducted at somewhat elevated temperatures, approximately 160°–210° C., and at autogenous pressures, using reaction times of 8–20 hours.

The products are useful as functional fluids or as intermediates.

9 Claims, No Drawings

FORMATION OF ALKYLSILANES

FIELD OF THE INVENTION

This invention pertains to preparation of organo derivatives of silane, $SiH_4$. More particularly, it pertains to use of alkali metal aluminates—also referred to herein as alkali metal tetraalkyls—to facilitate the reaction of silane and monoalkylsilanes with an olefin, or mixture of olefins. The alkali metal aluminum tetraalkyl can be used in two ways. As an example of the first way, silane and sodium aluminum tetraoctyl can be reacted in substantially equimolar amounts, using a solution of the sodium aluminum complex in octene-1 to facilitate contacting the reactants. The product is a mixture of the trioctyl- and dioctylsilanes, with the trioctylsilane being the major product. As a modification of this first method, an excess of either reactant can be used. For example, a 4:1 mole ratio of $NaAl(C_8H_{17})_4$ to silane has been reacted to increase the relative amount of trioctylsilane product with respect to the amount of dialkylated product.

As an example of the second way that alkali metal aluminates can be used in this invention, octene-1 and silane can be contacted with a catalytic quantity of sodium aluminum tetraalkyl, and a promoter quantity of a lithium halide. The product is dioctylsilane with a trace of trioctylsilane.

BACKGROUND OF THE INVENTION

According to the prior art, preparation of dialkyl and trialkylsilanes from silane is not easy to achieve. Prior art methods require strenuous conditions and/or afford low yields. For example, lower dialkylsilanes can be prepared from the monosubstituted compounds and the olefins by reacting them at 250°–450° C.; U.S. Pat. No. 2,786,862, Mar. 26, 1957. The monoalkylsilanes are first prepared from silane and olefins of 2–5 carbon atoms by heating at 25°–250° C. under pressure; U.S. Pat. No. 2,537,763, Jan. 9, 1951.

The methods of these patents appear to have been an advance in the art, for it was reported in the same time frame that "No method for the direct alkylation or alkoxylation of monosilane, $SiH_4$, has previously appeared in the literature"; Peake, et al, *J. Am. Chem. Soc.* 74, 1526 (1952). Furthermore, although Peake et al showed that phenyl sodium and lithium alkyls will react with silane, they were unable to alkylate silane using Grignard reagents, or phenylcalcium iodide, diphenyl calcium, or diethyl zinc. This work indicates there are material distinctions between various classes of organometallic reagents.

White et al, *J. Am. Chem. Soc.* 76, 3897 (1954) reacted ethylene and silane at 450°–510° C. by continuously circulating the gaseous reactants through the reaction zone. A mixture of products was formed including monoethyl-, diethyl-, and triethylsilane, as well as disilane, $Si_2H_6$, trisilane, $Si_3H_8$, and ethyldisilane $C_2H_5Si_2H_5$. With hindsight, one could expect such a complex product mixture since silane begins to decompose at 380° C.

SUMMARY OF THE INVENTION

This invention provides a means for alkylating silane and monoalkylsilanes under comparatively mild conditions. It also provides a method for forming dialkyl- and trialkylsilanes. In a first embodiment, reaction has been achieved when silane or a monoalkylsilane was contacted with sodium aluminum tetraalkyl in substantially equimolar amounts. Within this embodiment, reaction has also been achieved when the mole ratio of alkali metal aluminate to silane has been as high as 4 to 1. In this embodiment, the sodium aluminum complex can be used in solution in the olefin(s) from which the complex is derived.

In a second embodiment, the invention provides a means for alkylating silane using much less than stoichiometric amounts of $NaAlR_4$, say about 5 mole percent. When using $NaAlR_4$ as a catalyst in this manner, a lithium promoter is also used.

DESCRIPTION OF PREFERRED EMBODIMENTS

As indicated above, it is convenient to describe this invention in terms of two main embodiments. A first preferred embodiment is as follows:

A process for alkylating a silane reactant selected from the class consisting of silane, $SiH_4$, and monoalkylsilanes, $R'SiH_3$, wherein R' is a hydrocarbyl radical (i.e. a radical solely composed of carbon and hydrogen) containing from one to about 18 carbon atoms in a straight chain configuration, said process comprising contacting at a temperature of from about 160° to about 200° C., (i) said silane reactant, with
(ii) an alkali metal aluminate having the formula $MAlR_4$, wherein M is an alkali metal selected from lithium, sodium, or potassium, and each radical represented by R is a hydrocarbyl, straight chain, alkyl radical of about 4 to about 18 carbon atoms, whereby an alkyl radical R, becomes substituted for hydrogen in said silane reactant.

The second main preferred embodiment is:

A process for alkylating a silane reactant selected from the class consisting of silane and monoalkylsilanes wherein the alkyl group is solely composed of carbon and hydrogen and has up to about 18 carbon atoms, said process comprising contacting about equimolar amounts of said silane reactant and a straight chain, alpha olefin of from about 4 to about 18 carbon atoms, at about 160° to about 200° C., and in the presence of about 5–10 mole percent of an alkali metal aluminate having the formula $MAlR_4$ where M is selected from lithium, sodium, and potassium, and R is a straight chain hydrocarbyl, alkyl radical corresponding to said olefin, and in the presence of 0.1 to 0.25 mole percent, based on moles of silane reactant, of a lithium salt promoter selected from lithium halides and lithium carbonate.

The description of the invention in terms of the two main preferred embodiments set forth above is for purposes of illustration and is not in any way to be limiting. It is to be understood that this invention comprises a process for alkylating silane, and for further alkylating a monosilane, said process comprising contacting silane or a monoalkylsilane with an alkali metal aluminate under reaction conditions whereby an alkyl group is introduced into the silane or monoalkyl silane reactant. This process is somewhat selective since it appears to highly favor formation of products in which the silane atoms are bonded to at least one or two hydrogens. Stated another way, this invention preferentially yields dialkyl- and trialkylsilanes. The invention can be efficaciously employed to make trialkylsilanes by one main preferred embodiment, and dialkylsilanes by the other. Furthermore, as illustrated in the examples, silane can be added to reaction mixtures afforded by the invention to shift the product type "back" toward the monoalkylsilane from di- and trialkylsilane products.

In certain aspects, the invention can be considered to provide:

A process for preparing a dialkylsilane, said process comprising contacting silane under reaction conditions with a sodium aluminum tetraalkyl, whereby said dialkylsilane is produced. The invention can be conducted with a mole ratio of sodium aluminum tetraalkyl that makes the trialkylated silane the major product, with the dialkylsilane still being present.

This invention is primarily directed to the usage of olefins having from about 4 to about 18 carbon atoms. Compounds with greater or lesser numbers of carbons can also be used. Preferably, monoolefins of 6–12 carbons are used, more preferably these are alpha olefins. Thus, the olefin reactants can be illustrated by the compounds:

hexene-1
octene-1
decene-1
dodecene-1

It is not necessary that the olefins have an even number of carbons, however, these materials are commercially available by chain growth of ethylene, and also by isolation from natural products. Hence, they are preferred because of their availability. Olefins with an odd number of carbons can also be used. Mixtures of olefins, and pure, or substantially pure olefins can be used in this invention.

Olefins such as described above can be used as reactants according to one main embodiment of this invention. They can also be used as starting material for the preparation of the alkali metal aluminate used as a reactant in the other preferred main embodiment of this invention. Furthermore, they can be used as a solvent or reaction medium for the $MAlR_4$ reactant to facilitate contacting the reactants.

The alkali metal aluminate can be $LiAlR_4$, $NaAlR_4$, or $KAlR_4$. Mixtures of these materials can also be used. The sodium compounds are preferred because of their more ready availability. Preferably each group represented by R is the same.

The sodium aluminum tetraalkyl preferably contains alkyl group or groups corresponding to the olefin or olefins that are to be reacted with silane. The sodium aluminum complex can be used in a dissolved state; this is preferred since it facilitates contact with the gaseous reactant, silane. The complex can be dissolved in the olefin reactant and/or as stated above, the olefin from which it is derived.

As indicated above, the preferred reactants have the molecular formula $NaAlR_4$. Of these, compounds in which each of the R groups have 4–18 carbons are preferred, and those wherein the R groups each have 6–12 carbons are more preferred. The number of carbons in each alkyl group can be odd or even. Thus the $NaAlR_4$ complexes can be derived from the olefins mentioned above.

The materials in the reaction mixture are contacted under reaction conditions, i.e. under conditions that cause the reaction to take place at a convenient rate and not with an untoward amount of undesirable side reactions. Somewhat elevated temperatures are used, generally these are in the range from about 150° to about 250° C. In many instances, a temperature range of about 160° to about 200° C. is preferred. The process is facilitated by conducting it under pressure. Endogenous pressures are usually satisfactory; the materials are added to a pressure vessel, the vessel sealed, and the vessel then brought to desired reaction temperature. Pressures can be increased if desired by pressuring the vessel with nitrogen, argon or other inert gas. Although pressures in the range of from about 50 psig to about 300 psig are satisfactory; preferably, pressures from about 75 psig to about 150 psig are used. Higher or lower pressures can be employed if desired. Stirring, rocking or other means of agitating the non-gaseous material in the reaction vessel, facilitates contacting the reactants and is a preferred, but not critical, process expedient.

The time of reaction is not a truly independent variable, but is dependent at least to some extent on the other reaction conditions employed. In general, higher pressures and temperatures give shorter reaction times. Usually the reaction is complete in less than two days (48 hours). It is convenient in many instances to run the reaction overnight; when using preferred reaction conditions the reaction is usually complete in 8–20 hours.

The reaction can be conducted in the presence of an inert ingredient or ingredients that do not materially interfere with the course of the reaction. Thus for example, the process may be conducted in the presence of an inert liquid paraffinic hydrocarbon such as octane, or decane, or similar substance. Such substances may be used to increase the volume of the liquid phase and thereby facilitate contacting the reactants. Furthermore, a higher paraffin can be added to the reaction mixture to serve as an internal standard for gas chromatographic analysis. As already stated, the reaction may also be run in the presence of olefin in excess of any olefin employed as a reactant. Thus, an olefin selected from those mentioned above can be employed as solvent and/or as a reactant in accordance with the teachings herein.

In general, the process is conducted by admixing the reactants in a pressure reaction vessel and then bringing the mixture to the desired reaction temperature and pressure. As stated above, when the sodium aluminum tetraalkyl is used as a reactant it can be contained in the olefin or olefins from which it is derived.

The reactants can be combined in any relative quantity, i.e. molar ratio, that will permit the reaction to proceed as desired. By simple experiment a skilled practitioner can determine if a particular molar ratio to be employed will allow the reaction to take place as desired and in accordance with one of the embodiments set forth herein. For example, as set forth more fully below, a mole ratio of 4 moles of $NaAlR_4$ per mole of $SiH_4$ can be used to favor the formation of $R_3SiH$. On the other hand, if one mole portion of each reactant is utilized, then in a system illustrated in the examples, the product ratio is about one mole portion of di-substituted product $R_2SiH_2$, to about 1.5–1.7 mole portions of tri-substituted product, $R_3SiH$. In essence, the tri-substituted product is favored when higher portions of $NaAlR_4$ are employed in the reaction mixture and, alternatively, formation of the di-substituted product is made more likely by increasing the relative amount of silane.

As shown in the Examples, and as discussed above, a process of this invention can be carried out by contacting a mixture of $SiH_4$, $NaAlR_4$ and olefin, where the olefin corresponds to the alkyl group in the complex metal reactant. For example, the $NaAlR_4$ ingredient may be dissolved in the olefin as in the example below where sodium aluminum tetraoctyl, NaAl($C_8H_{17}$)$_4$, is dissolved in octene-1, $C_8H_{16}$. In these instances, there are conceptually two reaction mechanisms that might be involved. First, it is possible that all the alkyl groups in the $R_2SiH_2$ and $R_3SiH$ products are derived from the alkyl groups in the NaAlR$_4$ species that is present. Alternatively, the process might involve, to a greater or lesser extent, reaction between the olefin and the SiH$_4$ (or intermediate silane product) promoted or catalyzed by the NaAlR$_4$ present. Rigorous experimentation has not been conducted to determine what mechanism or mechanisms are involved, or if more than one is involved and if so, to what extent each takes place. Thus, it is to be understood that the instant invention is not limited by any description of the possible chemical mechanism(s) by which the reaction might occur.

As illustrated by an example below, the process can be conducted by reacting an alkylsilane, $R^2SiH_3$ wherein $R^2$ is a lower alkyl such as hexyl. By the process of this invention these materials can be transformed, to some extent into such materials as $R^2SiR_3$ wherein the radicals represented by R are alike or different and have 6 or more carbon atoms. These materials offer promise as functional fluids, e.g. hydraulic fluids or high technology lubricants; confer U.S. Pat. No. 4,367,343. In some instances the reaction of this invention yields a compound, $R_2SiH_2$ or $R_3SiH$. These are useful in their own right as chemical intermediates.

As stated above, this invention provides a method in which an olefin (or olefins) are reacted with SiH$_4$ using NaAlR$_4$ in catalytic amount and a lithium compound as a promoter. In this embodiment, the NaAlR$_4$ complex is used in amount substantially less than stoichiometric. For example, the NaAlR$_4$ compound can be used in an amount less than 10 mole percent, based on the amount of silane used. Generally speaking, the NaAlR$_4$ complex (when used as a catalyst) is employed in an amount equivalent to about 5 to about 10 mole percent based on the silane reactant. Greater or lesser amounts can be employed. When the NaAlR$_4$ is used as a catalyst, a promoter quantity of lithium compound is used. Lithium chloride has been found to act as a promoter and it suggests use of other lithium salts such as the other halides, e.g. LiBr and materials such as Li$_2$CO$_3$. Generally, from 0.1 to about 0.25 mole percent (based on silane) of the lithium compound is used. Greater or lesser amounts can be employed.

With regard to the catalyst and the promoter, the practitioner will want to employ enough of each to cause the reaction to proceed in an efficacious manner. However, the amounts employed are preferably not substantially above what is required. An excess can be wasted and unnecessarily increases the amount of material to be discarded after use.

It appears the rate determining step is the formation of the monoalkylated product, and it also appears that substance reacts comparatively easily to form the dialkylated product. The formation of the trialkylated product is more difficult.

The reaction can be stopped at a comparatively early stage and the presence of the monoalkylated product can be detected. It can be isolated if that product is desired. If the intent is to make the mono-product, the reaction time need not be as long as given above, and can be about 5-10 hours or less. These products are useful as intermediates.

EXAMPLE 1

A 48.2 gram portion of a solution of NaAlR$_4$, i.e. NaAl($C_8H_{17}$)$_4$, in octene-1 containing about 52.1 wt. percent NaAlR$_4$ (i.e. 0.05 mole) NaAl($C_8H_{17}$)$_4$ was added to a 300 ml. stainless steel autoclave. After the autoclave was sealed, it was purged by bubbling in nitrogen for 5 minutes. Thereafter, 0.05 mole of silane (1.6 gram) was added. No reaction was observed (i.e. no drop in pressure was observed) after 4 hours of stirring at room temperature. No drop in pressure occurred after stirring at 50° C. for one hour. The reaction mass was heated to 100° C. and left stirring overnight. The reaction mass was then cooled to room temperature and left over the weekend. No reaction was observed.

Next, the silane was vented and 25 ml. of diethyl ether added to the autoclave. The autoclave was then sealed, purged with nitrogen for 5 minutes and a second batch of 0.05 mole of silane added.

No reaction occurred after one hour of stirring at room temperature. The temperature was taken up to 190° C. causing an increase in pressure. After stirring for two hours at 190° C. the vessel contents were cooled to room temperature. Then 100 ml. of 10% HCl was carefully added. The resultant mass was stirred and left to sit overnight.

The organic phase was separated, washed twice with saturated, aqueous NaHCO$_3$ and once with water. The organic phase was then dried over CaCl$_2$.

Low boiling components were distilled using a rotary evaporator. Gas phase chromatographic/mass spectrographic analysis demonstrated that the weight ratio of H$_2$Si($C_8H_{17}$)$_2$ to HSi($C_8H_{17}$)$_3$ was 1 to 1.67.

EXAMPLE 2

The following materials were mixed in a 300 ml. autoclave:

| | | | |
|---|---|---|---|
| lithium chloride | 0.0023 mole | 4.6 mole % | (0.1 g) |
| sodium aluminum tetraoctyl* | 0.05 mole | 25.1 g. | |

*in 48 grams of a 52% solution in octene-1

The vessel was purged with nitrogen and 1.6 grams (0.05 mole) of silane was added. The vessel was heated to 190° C. and left stirring overnight. A pressure drop was observed prior to reaching 190° C. After 16 hours at 190° C., the reaction mixture was cooled and unreacted silane vented. The reaction mixture was then hydrolyzed with 100 ml. of a 10% HCl solution, and the organic phase separated. The organic phase was washed twice with 10% HCl, and then with water. After drying over CaCl$_2$, a sample was taken and shown to comprise dioctylsilane ($C_8H_{17}$)$_2$SiH$_2$ and trioctyl silane ($C_8H_{17}$)$_3$SiH, in a weight ratio of 1 to 1.57, respectively.

The above reaction can be carried out at a temperature within the range of 160°-200° C. The lithium chloride was employed as a possible catalyst for the reaction. Its use suggests employment of it, and/or other similar substances such as lithium bromide and lithium carbonate in amounts of about 2 to about 10 mole percent based on silane.

EXAMPLE 3

By substantially following the same procedure given in the above examples, n—$C_6H_{13}SiH_3$(5.8 grams, 0.05 mole) and 48.2 grams of an octene solution containing 52% of NaAl(C$_8$H$_{17}$)$_4$ were reacted at 170°±3° C. for 25.5 hours. The resultant mixture was cooled and allowed to stand over the weekend at room temperature.

After hydrolysis, gas chromatographic/mass spectrophotometric analysis (GC/MS) showed the presence of dioctylhexylsilane and hexyloctylsilane.

EXAMPLE 4

Following the general procedure in the above examples:

| | | |
|---|---|---|
| SiH$_4$ | 3.2 g | 0.1 mole |
| octene-1 | 44.8 g | 0.4 mole |
| NaAlH$_4$ | 5.4 g | 0.1 mole |
| LiCl | 0.1 g | 0.0024 mole | were placed in a 300 ml autoclave and reacted at 190° C. overnight. The reaction was cooled to room temperature. A sample was taken and after hydrolysis, GC analysis showed the presence of trioctyl- and dioctylsilane (minor product).

In this experiment a pressure increase was noted during the course of the reaction, and it is believed this resulted from the evolution of hydrogen formed by decomposition of NaAlH$_4$.

The LiCl was employed in this experiment as a potential catalyst for the reaction. It suggests the use of other lithium halides and diverse lithium salts such as Li$_2$CO$_3$.

The process of the example can be employed using butene-1, hexene-1, decene-1, dodecene-1, tetradecene-1, hexadecene-1 and octadecene-1 as a reactant and reaction temperatures in the range of 160°-200° C. Similar results are obtained, i.e. the product contains R$_2$SiH$_2$ and R$_3$SiH wherein R is an alkyl radical corresponding to the olefin employed as a reactant.

EXAMPLE 5

In this example:

| | | |
|---|---|---|
| NaAl(C$_8$H$_{17}$)$_4$ | 12.55 g | 0.025 mole |
| octene-1 | 44.8 g | 0.4 mole |
| SiH$_4$ | 3.2 g | 0.1 mole |
| LiCl | 0.1 g | 0.0024 mole |
| tetradecane | 2.0 g | (internal standard) | were added to a 300 ml. stainless steel autoclave and heated overnight at 170°-175° C. with constant stirring. After 17 hours all the silane had reacted, and after cooling to room temperature, the reaction mixture was charged with an additional 0.1 mole of SiH$_4$. After 4 hours at 170°-175° C. this silane was also consumed. The autoclave was again cooled to room temperature and 70 g (0.5 mole) of decene-1 was added through the autoclave dipleg. (A slight vacuum was created in the autoclave.) The reaction was heated to 170° C. overnight. GC/MS analysis of a sample showed the presence of C$_{10}$ alkylation; H$_2$Si(C$_8$H$_{17}$)(C$_{10}$H$_{21}$) was present along with H$_2$Si(C$_{10}$H$_{21}$)$_2$.

The first steps of the reaction sequence can be summarized as follows:

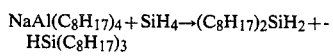

NaAl(C$_8$H$_{17}$)$_4$+SiH$_4$→(C$_8$H$_{17}$)$_2$SiH$_2$+-HSi(C$_8$H$_{17}$)$_3$ (The process was an essentially complete reaction; the yield was essentially quantitative for the dialkyl product, a trace of trialkylsilane was produced.)

The reaction mixture was left stirring overnight at 170°-175° C. It was then transferred (after cooling) to a one liter autoclave and one mole each of octene-1 and decene-1 were added. The resultant reaction mass was stirred overnight. The intended reaction temperature was 175° C.; however there was an equipment failure (the cooling device) and it is believed the reaction temperature exceeded 200° C. There was not much evidence of formation of a trialkylated derivative, and it is believed the unintended higher temperature decomposed the aluminate.

EXAMPLE 6

Into a liter autoclave, the following materials were added:

| | | |
|---|---|---|
| octene-1 | 1 mole | 112 g |
| decene-1 | 1 mole | 140 g |
| silane | 0.5 mole | 16 g |
| LiCl | 0.0024 mole | 0.1 g |
| NaAl(C$_8$H$_{17}$)$_4$ | 0.0252 mole* | 12.63 g |

The autoclave was heated to 170°-175° C. and stirred overnight. After 17 hours of reaction, the pressure had dropped to 10 psig indicating substantially all the silane had reacted. A small sample was hydrolyzed and the product was shown to mainly comprise R$_2$SiH$_2$ (R=C$_8$H$_{17}$ or C$_{10}$H$_{21}$). Another 0.1 mole of SiH$_4$ was added and some soon reacted showing reactivity of the aluminate. Remaining silane was vented and the reaction mass left to stir overnight (170° C.) to attempt trialkylation. After 24 hours, no additional trialkyl species was observed in the reaction mass indicating the third alkyl group is difficult to add, probably because of steric interference. This experiment confirmed the ability of NaAlR$_4$ species to act in catalytic quantities and cause silane to be alkylated.

The process of this example yielded a mixture of products comprising H$_2$Si(C$_8$H$_{17}$)$_2$, H$_2$Si(C$_8$H$_{17}$)(C$_{10}$H$_{21}$) and H$_2$Si(C$_{10}$H$_{21}$)$_2$ mole ratio of substantially 1:2:1, respectively.

The process yields similar results when another metal aluminate, NaAlR$_4$, LiAlR$_4$, or KAlR$_4$ is used, wherein R is selected from butyl, hexyl, decyl, dodecyl, tetradecyl or octadecyl, and the amount of metal aluminate is from 2 to 10 mole percent based on the amount of the silane reactant.

The process also yields similar results when two olefins are selected from butene-1, hexene-1, octene-1, decene-1, dodecene-1, tetradecene-1, hexadecene-1 and octadecene-1 to give a reaction mixture differing from the octene-1 and decene-1 mixture used in the example. The mole ratio of the two olefins can vary from 10 to 90 mole percent of either. The process can be conducted at a temperature of 160°-200° C. with or without the lithium chloride. When employed, the chloride is used in an amount equal to 0.1 to 0.25 mole percent based on silane.

EXAMPLE 7

To a 300 ml. autoclave the following ingredients were added:

| | | |
|---|---|---|
| NaAl(C$_8$H$_{17}$)$_4$ | 0.025 mole | 12.6 g |
| SiH$_4$ | 0.025 mole | 0.8 g |
| octene-1 | 0.4 mole | 44.8 g |
| lithium chloride | 0.0024 mole | 0.1 g |

After stirring for 18.5 hours at 175° C., a sample showed $(C_8H_{17})_2SiH_2$, 52.3 area percent, and $(C_8H_{17})_3SiH$, 3.6 area percent. After addition of 0.0125 moles of silane and reaction for two hours and 30 minutes at 170°–175° C., a sample showed the presence of monoalkylated silane, $C_8H_{17}SiH_3$. After stirring an additional 7 hours, vapor phase chromatographic (VPC) analysis of the sample showed the presence of:

| | |
|---|---|
| $C_8H_{17}SiH_3$ | 7 area % |
| $(C_8H_{17})_2SiH_2$ | 50 area % |
| $(C_8H_{17})_3SiH$ | 3 area % |

Subsequently, an attempt to catalyze further reaction with diisopropylamine did not show any increase in trialkylsilane formation.

EXAMPLE 8

The following were charged to a 300 ml. stainless steel autoclave:

| | | |
|---|---|---|
| $HSi(C_8H_{17})_3$ | 0.01 mole | 3.68 g |
| $NaAl(C_{10}H_{21})_4$ | 0.01 mole | 6.14 g |
| $SiH_4$ | 0.01 mole | 3.2 g |
| $C_{14}H_{30}$* | 0.01 mole | 1.98 g |
| decene-1 | 0.1 mole | 14 g |

*internal standard

After stirring at 170°–175° C. for 3 hours and 20 minutes, a VPC analysis did not show the presence of $H_2Si(C_8H_{17})_2$ or $HSi(C_8H_{17})_2(C_{10}H_{21})$.

To the reaction mixture was then added 0.01 mole of trioctylaluminum and the resultant mixture heated for 170°–175° C. for 16 hours. VPC analysis showed the presence of mixed trialkylsilanes, $HSi(C_{8-10})_3$. The presence of the mixed trialkylsilanes may be due to the addition of the trioctylaluminum.

EXAMPLE 9

To a 300 ml. stainless steel autoclave was added:

| | | |
|---|---|---|
| $NaAl(C_8H_{17})_4$* | 0.09 mole | 44.6 g |
| $SiH_4$ | 0.0225 mole | 0.72 g |
| $Al(C_8H_{17})_3$ | 0.0023 mole** | 0.82 g |

*53.55% solution in octene-1
**10 mole % based on silane

The mixture was heated to 170°–175° C. overnight, and after 17 hours, the mole ratio of $(C_8H_{17})_2SiH_2$ to $(C_8H_{17})_3SiH$ was 2:1. Little change was observed after one hour at 190° C. The temperature was increased to 220° C. for 5 hours. A VPC analysis showed (area %) that the ratio of $HSiR_3/H_2SiR_2$ was 20:1. There was an increase in hexadecene probably due to the high reaction temperature.

The reaction was cooled to room temperature and 0.1 mole of silane and 0.4 mole of octene-1 was added. The temperature was increased to 220° C. for 5 hours. A VPC analysis showed (area %) the ratio of $HSiR_3/H_2SiR_2$ was 20:1. There was an increase in hexadecene probably due to the high reaction temperature.

The reaction was cooled to room temperature and 0.1 mole of silane and 0.4 mole of octene-1 was added. The temperature was increased to 220° C., and left overnight. After 17 hours at 220° C., VPC analysis showed the following mixture ratios:

| Mixture | Ratio |
|---|---|
| $(C_8H_{17})_3SiH/(C_8H_{17})_2SiH_2$ | 15:1 |
| octene/$C_8H_{17}SiH_3$ | 3:1* |

*This is the same ratio as was noted prior to the addition of the 0.1 mole charge of silane.

The formation of the hexadecene in the above example suggests that the formation of such higher boiling products can be used by a skilled practitioner as an indication that a side reaction is taking place. In some instances the practitioner will wish to lower the reaction temperature to reduce the rate of formation of the higher boiling product.

The products of this invention can be used as chemical intermediates. For example, the dialkylsilanes can be reacted with methanol and the product of that reaction used to form silicones.

The products of this invention can be utilized as reducing agents; for example, they can be used to reduce alkyl halides such as the chlorides to the paraffins.

We claim:

1. A process for alkylating a silane reactant selected from the class consisting of silane, $SiH_4$, and monoalkylsilanes, $R'SiH_3$, wherein $R'$ is a hydrocarbyl radical containing from one to about 18 carbon atoms in a straight chain configuration,
said process comprising contacting at a temperature of from about 160° to about 200° C.,
(i) said silane reactant, with
(ii) an alkali metal aluminate having the formula $MAlR_4$, wherein M is an alkali metal selected from lithium, sodium or potassium, and each radical represented by R is a hydrocarbyl, straight chain alkyl radical of about 4 to about 18 carbon atoms,
whereby an alkyl radical R, becomes substituted for hydrogen in said silane reactant.

2. A process of claim 1 wherein said process is conducted in a sealed, pressure reaction vessel under autogeneous pressure.

3. A process of claim 2 wherein said aluminate is a sodium aluminum tetraalkyl and is employed admixed with an alpha olefin corresponding to a radical R within said aluminate.

4. A process of claim 3 wherein the mixture of olefin and alkali metal aluminate is a solution containing about equal amounts by weight of said olefin and said aluminate.

5. A process of claim 4 wherein the silane reactant and aluminate are reacted in substantially equimolar amounts.

6. A process of claim 4 wherein silane and sodium aluminum tetraoctyl are reacted and form a mixture of $H_2Si(C_8H_{17})_2$ and $HSi(C_8H_{17})_3$.

7. A process of claim 4 wherein said silane reactant is n—$C_6H_{13}SiH_3$ and said aluminate is $NaAl(C_8H_{17})_4$ and the product comprises a mixture of $H(C_6H_{13})(C_8H_{17})_2Si$ and $H_2(C_6H_{13})(C_8H_{17})Si$.

8. A process for alkylating a silane reactant selected from the class consisting of silane and monoalkyl silanes wherein the alkyl group is solely composed of carbon and hydrogen and has up to about 18 carbon atoms, said process comprising contacting (a) said silane reactant, and (b) a straight chain, alpha olefin of from about 4 to about 18 carbon atoms, in about equimolar amounts and at about 160° to about 200° C. in the presence of about 5–10 mole percent of an alkali metal aluminate having the formula $MAlR_4$ where M is selected from lithium, sodium, and potassium and R is a straight chain hydrocarbyl alkyl radical corresponding to said olefin, and in the presence of 0.1 to 0.25 mole percent, based on the silane reactant, of a lithium salt selected from lithium halides and lithium carbonate.

9. A process of claim 8 wherein silane is reacted with octene-1 using sodium aluminum tetraalkyl as a catalyst and lithium chloride as a promoter.

* * * * *

UNITED STATES PATENT AND TRADEMARK OFFICE
CERTIFICATE OF CORRECTION

PATENT NO. : 4,670,574

DATED : JUNE 2, 1987

INVENTOR(S) : Arcelio J. Malcolm et al

It is certified that error appears in the above-identified patent and that said Letters Patent is hereby corrected as shown below:

Column 7, line 17, "reaotion" should read -- reaction --.

Column 8, line 21 is blank and should read
-- * 5.0 mole percent based on silane. --.

Signed and Sealed this

Twenty-seventh Day of October, 1987

Attest:

DONALD J. QUIGG

Attesting Officer

Commissioner of Patents and Trademarks